US009823224B2

(12) United States Patent
Buelsing et al.

(10) Patent No.: US 9,823,224 B2
(45) Date of Patent: Nov. 21, 2017

(54) WELD INSPECTION METHOD AND SYSTEM

(71) Applicant: Caterpillar Inc., Peoria, IL (US)

(72) Inventors: Michael T. Buelsing, Peoria, IL (US); Jean O. Bridge, Morton, IL (US); Leon Adcock, Chillicothe, IL (US); Gregory H. Dubay, Carlock, IL (US); Dong Fei, Peoria, IL (US); Donald Stickel, Chillicothe, IL (US)

(73) Assignee: Caterpillar Inc., Peoria, IL (US)

( * ) Notice: Subject to any disclaimer, the term of this patent is extended or adjusted under 35 U.S.C. 154(b) by 92 days.

(21) Appl. No.: 14/936,388

(22) Filed: Nov. 9, 2015

(65) Prior Publication Data

US 2017/0131220 A1    May 11, 2017

(51) Int. Cl.
*G01N 21/00* (2006.01)
*G01N 29/06* (2006.01)
*G01N 29/26* (2006.01)
*G01N 29/265* (2006.01)

(52) U.S. Cl.
CPC .......... *G01N 29/06* (2013.01); *G01N 29/069* (2013.01); *G01N 29/262* (2013.01); *G01N 29/265* (2013.01); *G01N 2291/2675* (2013.01)

(58) Field of Classification Search
CPC .............. G01N 21/956; G01N 21/954; G01N 21/95684; G01N 21/8851; G01N 2021/8858; G01N 2021/8861; G01N 2021/8864; G01N 2021/8806; G01N 21/93; G01N 21/95692; G01N 2021/8887; G01N 29/0618; G01N 29/043; G01N 29/06; G01N 29/069; G01N 29/262; G01N 29/265; G01N 2291/2675; G02B 26/10
See application file for complete search history.

(56) References Cited

U.S. PATENT DOCUMENTS

| 5,337,611 | A | * | 8/1994 | Fleming | G01N 29/0618 73/622 |
|---|---|---|---|---|---|
| 8,616,062 | B2 | | 12/2013 | Kono et al. | |
| 2014/0058266 | A1 | | 2/2014 | Call et al. | |
| 2014/0168413 | A1 | * | 6/2014 | Lee | G01N 21/95684 348/90 |
| 2015/0039245 | A1 | * | 2/2015 | Langlois | G01N 29/043 702/39 |
| 2016/0069820 | A1 | * | 3/2016 | Bueno | G01N 21/954 356/607 |

* cited by examiner

*Primary Examiner* — Jamil Ahmed

(57) ABSTRACT

A system for inspecting a weld on a component where the weld has a plurality of cross-sections includes a camera disposed above the weld that optically senses a weld position. A projector disposed above the weld projects on to the component along a length of the weld position a primary scan path with a primary scan path start point and a primary scan path end point. An imaging probe scans the weld as the imaging probe moves from the primary scan path start point to the primary scan path end point to generate a plurality of 2D cross-sectional images of the weld corresponding to the cross-sections of the weld, the imaging probe having a position and skew angle that vary as the imaging probe moves. Each 2D cross-sectional image of the weld is optically encoded with a respective imaging probe position and a respective imaging probe skew angle.

19 Claims, 6 Drawing Sheets

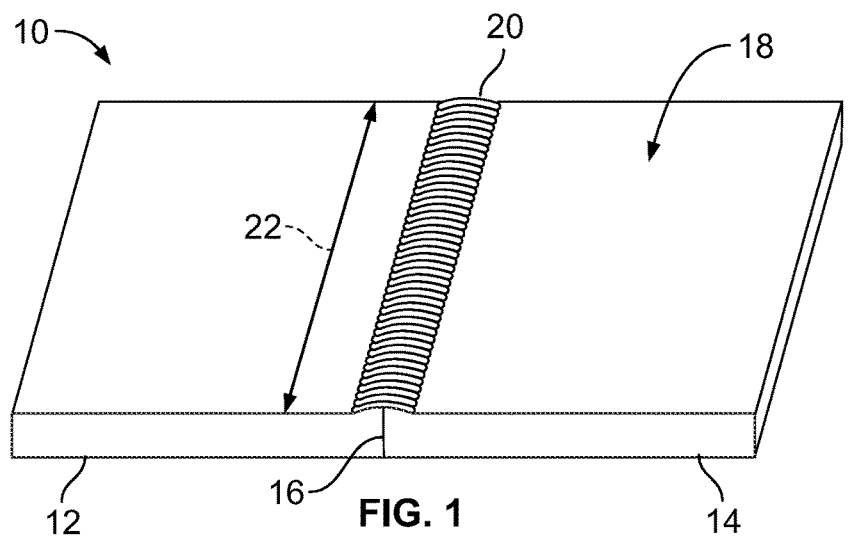
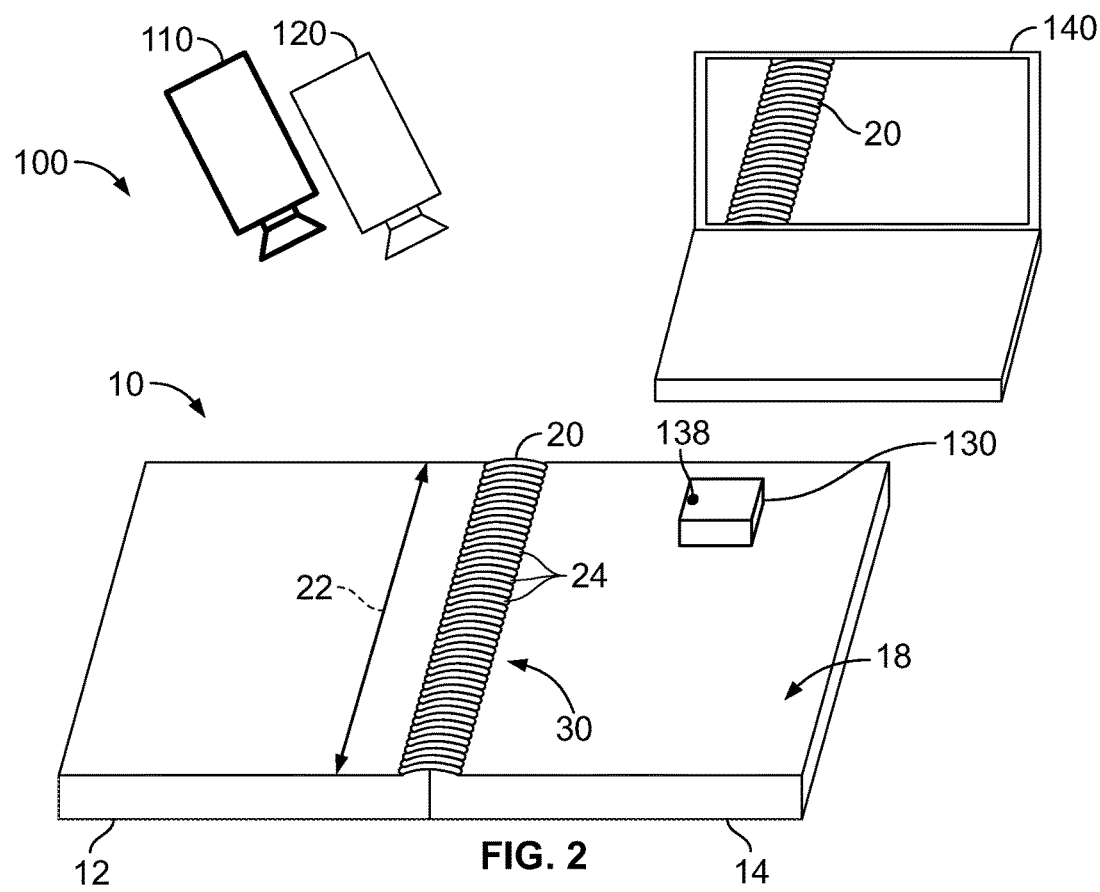

US 9,823,224 B2

WELD INSPECTION METHOD AND SYSTEM

TECHNICAL FIELD

The present disclosure relates generally to inspecting welds and, more particularly, to objective, semi-automated weld inspection methods and systems.

BACKGROUND

A weld may include one or more discontinuities. Welds are often manually inspected by human inspectors who make a subjective determination about whether a discontinuity in the weld may cause the weld to fail. If the discontinuity is unlikely to cause the weld to fail, it is identified by the inspector as an acceptable discontinuity. If, however, the discontinuity is likely to cause the weld to fail, it is identified by the inspector as a rejectable discontinuity, also known as a defect. An example of a rejectable discontinuity or defect may be a lack of fusion between two parts that are welded together. Upon determining that a given discontinuity is rejectable, the inspector may mark the location of the rejectable discontinuity on the weld so that a welder may fix the weld accordingly. There is typically no record as to why the weld was considered to be defective by the human inspector.

More recently, welds can be inspected using computer imaging techniques. Significant advances have been made in the field of two-dimensional or "2D" imaging for non-destructive weld evaluation. However, the technology is still limited both by the lack of a convenient manner of encoding the location of the 2D imaging information relative to the weld of interest, and by the subjective nature of the image interpretation, which is performed by a human inspector.

U.S. Pat. No. 8,616,062 describes a method of ultrasonically inspecting a test object using an immersion technique. However, the method does not alleviate the problem of providing a convenient means of gathering relevant encoded ultrasonic data.

U.S. Patent Application Publication No. 2014/0058266 describes an ultrasound imaging system memory architecture. However, the system does not provide an objective, repeatable assessment of weld discontinuities.

SUMMARY

In one aspect, the present disclosure describes a method of inspecting a weld on a component where the weld has a plurality of cross-sections. The method includes optically sensing a weld position of the weld with respect to the component and projecting on to the component along a length of the weld position a primary scan path with a primary scan path start point and a primary scan path end point. The weld is then scanned by moving an imaging probe from the primary scan path start point to the primary scan path end points as to generate a plurality of 2D cross-sectional images of the weld that correspond to the plurality of cross-sections of the weld. The imaging probe has an imaging probe position with respect to the weld and an imaging probe skew angle with respect to the weld, both of which vary as the probe moves along the primary scan path. Each of the plurality of 2D cross-sectional images of the weld is optically encoded with a respective imaging probe position and a respective imaging probe skew angle of the imaging probe.

In another aspect, the present disclosure describes a system for inspecting a weld on a component where the weld has a plurality of cross-sections. The system includes a camera disposed above the weld that optically senses a weld position of the weld with respect to the component. A projector disposed above the weld projects on to the component along a length of the weld position a primary scan path with a primary scan path start point and a primary scan path end point. An imaging probe scans the weld as the imaging probe moves from the primary scan path start point to the primary scan path end point so as to generate a plurality of 2D cross-sectional images of the weld that correspond to the plurality of cross-sections of the weld.

In yet another aspect, the present disclosure describes a method of inspecting a weld on a component. The method includes projecting on to the component a scan path with a scan path start point and a scan path end point and scanning the weld by moving an imaging probe from the scan path start point to the scan path end point so as to generate a cross-sectional image of one or more cross-sections of the weld. The imaging probe has an imaging probe position with respect to the weld and an imaging probe skew angle with respect to the weld, both of which vary as the probe moves along the scan path. Each of the cross-sectional images is optically encoded with a respective imaging probe position and a respective imaging probe skew angle of the imaging probe.

BRIEF DESCRIPTION OF THE DRAWINGS

FIG. 1 is a perspective view of two parts that have been welded together to form a component.

FIG. 2 is a schematic perspective view of an inspection system according to the present disclosure.

DETAILED DESCRIPTION

Figure 3:
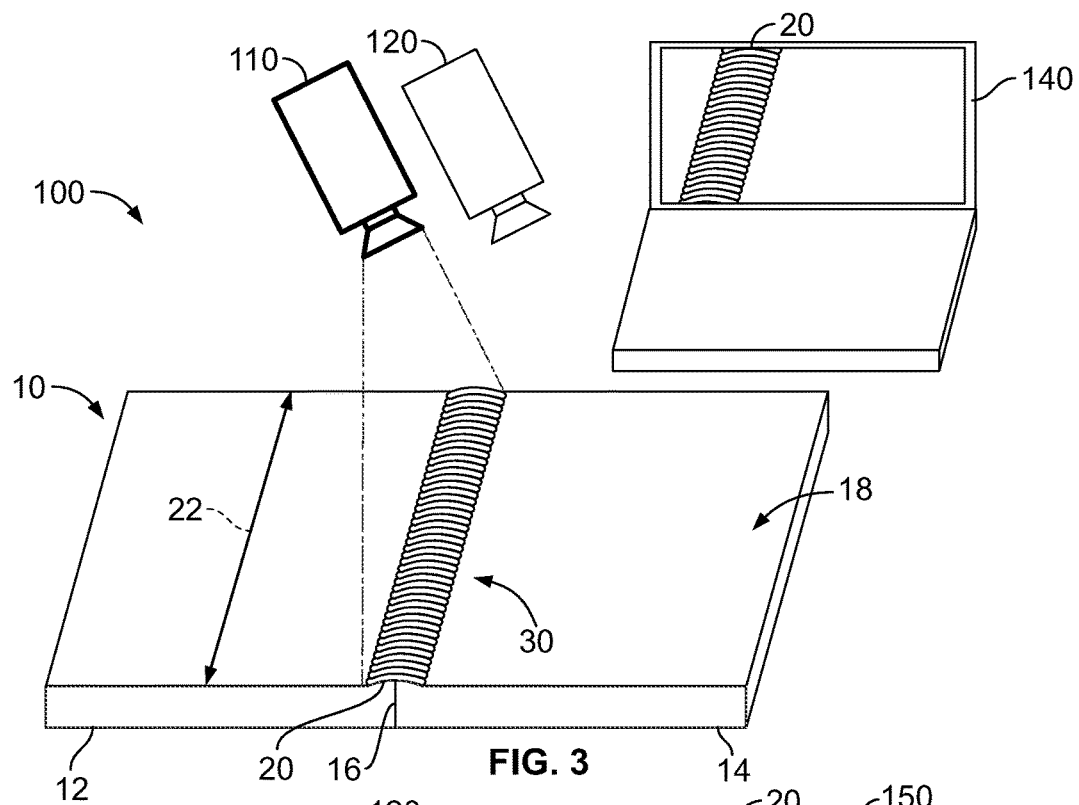
FIG. 3 is a schematic perspective view of the inspection system of FIG. 2 optically sensing a location of the weld with respect to the component of FIG. 1.

The present disclosure relates to objective, semi-automated weld inspection methods and systems. FIG. 1 illustrates an exemplary component 10 that includes a first part 12 and a second part 14. First part 12 and second part 14 are welded together with a weld 20 along a weld joint 16. Weld 20 has a length 22. First part 12 and second part 14 can be welded together to form component 10 either by a welder who manually welds first part 12 to second part 14 or by a welding machine that automates the welding of first part 12 to second part 14. In either case, it is possible that weld 20 may have one or more rejectable discontinuities or defects, which are undesirable in that they may undermine the strength of weld 20, comprising the integrity of component 10. An inspection of weld 20 may be used to ensure that weld 20 does not include any rejectable discontinuities. Component 10 shown in the figures is one example configuration of a welded component. It is contemplated that component 10 could have other configurations.

FIG. 2 shows an inspection system 100 for determining whether weld 20 has one or more discontinuities. Inspection system 100 includes a camera 110 and a projector 120. Camera 110 may be mounted such that it can view the entirety of weld 20, while projector 120 may be mounted so as to be able to project a projection on to component 10 that is viewable by an operator of inspection system 100. For example, camera 110 and projector 120 may be mounted above component 10 and weld 20. The illustrated inspection system 100 also includes an imaging probe 130 for scanning weld 20 to assist in determining whether weld 20 has one or more discontinuities. Inspection system 100 may also include a computer 140 that is connected to camera 110, projector 120, and imaging probe 130. The connections between the components of inspection system 100 could be wired or wireless.

Camera 110 may be a digital camera and be capable of capturing still images and/or video. Camera 110 may be controlled by one or more programs run on computer 140 and may provide input to and receive output from computer 140 in connection with the operation of inspection system 100. Camera 110 may be used to optically sense a weld position 30 of weld 20 with respect to component 10. Camera 110 may also be used to optically sense an orientation of imaging probe 130 with respect to weld 20 during the scanning of weld 20 and to optically encode that information to generate a plurality of 2D images of the cross-sections 24 of weld 20, as explained in further detail below with respect to FIGS. 5-7.

Projector 120 may be used to project projections on to component 10 and weld 20. Projector 120 may be controlled by one or more programs run on computer 140 and may provide input to and receive output from computer 140 in connection with the operation of inspection system 100. For example, computer 140 may be configured to control projector 120 so that it projects on to component 10 a scan path for imaging probe 130, such as primary scan path 150 (shown in FIG. 4), along which an operator of inspection system 100 moves imaging probe 130 to scan weld 20. In this manner, the operator of inspection system 100 is provided with a visual indicator of where to move imaging probe 130 on component 10 with respect to weld 20 in order to scan weld 20.

Figure 4:
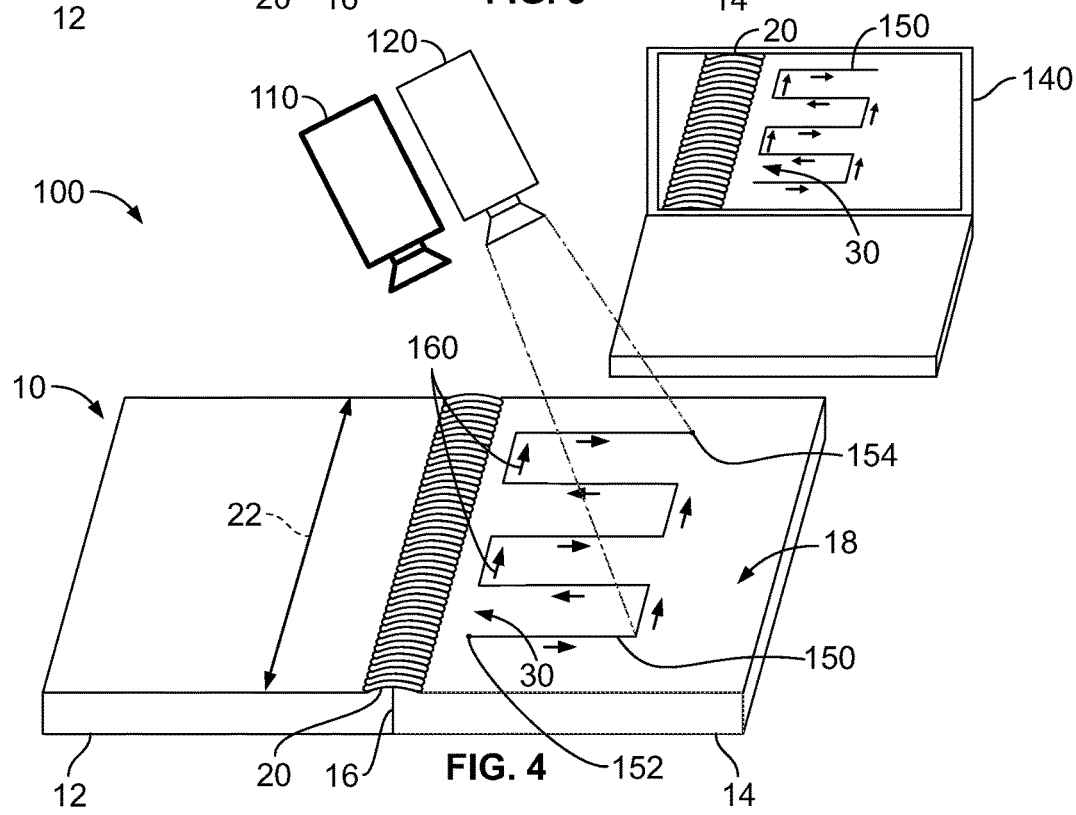
FIG. 4 is a schematic perspective view of the inspection system of FIG. 2 projecting a scan path on to the component of FIG. 1.

The scan path can be one of a number of shapes or patterns. For example, primary scan path 150 shown in FIG. 4 is a raster-type scan path. A raster-type primary scan path 150 prompts the operator of inspection system 100 to move imaging probe 130 farther away from weld 20, then parallel to weld 20, then closer to weld 20, then again parallel to weld 20. This pattern would then be repeated until operator of inspection system 100 had moved the imaging probe 130 along the length 22 of weld 20. The scan path projected on to component 10 by projector 120 could also be a linear path that extends along and parallel to length 22 of weld 20, such as secondary scan path 170 (shown in FIG. 8).

The shape or pattern of a scan path projected on to component 10 by projector 120, such as primary scan path 150, could be a function of a number of parameters, such as length 22 of weld 20 or component 10, the shape or configuration of weld 20, the geometry of weld joint 16, the types of discontinuities in which the operator of inspection system 100 is most interested in detecting, and/or the requirements of any codes or specifications with which weld 20 and component 10 must conform, among other factors. If, for example, component 10 were a cylindrical pipe, a scan path could be projected on to component 10 by projector 120 so as to follow a curvature of the cylindrical pipe. Projector 120 can also project scan paths on either side of weld 20. The shape or pattern of the scan path projected on to component 10 by projector 120 can be determined by one or more programs running on computer 140, or it could be manually programmed by the operator of inspection system 100 or the operator's supervisor.

Referring again to FIG. 2, imaging probe 130 is used to scan weld 20 to help determine whether weld 20 includes one or more discontinuities. Imaging probe 130 may be, for example, an ultrasonic transducer, and in particular a manual contact phased array ultrasonic transducer. As a general matter, weld 20 may have up to n different cross-sections 24 across its length 22. Although cross-sections 24 are shown as corresponding to the slag folds of weld 20, it will be understood by persons of skill in the art that this representation is merely a simplification to aid in the explanation of the function of imaging probe 130 and how it samples along the length 22 of weld 20. More particularly, imaging probe 130 is used to sample each cross-section 24 so as to generate a plurality of 2D cross-sectional images of weld 20, each of which corresponds to a single cross-section 24 of weld 20. The functionality of imaging probe 130 will be explained in further detail below in connection with FIG. 5.

Computer 140 is a general purpose computer capable of controlling inspection system 100 and interfacing with the various components of inspection system 100, including camera 110, projector 120, and imaging probe 130. Computer 140 may also display information regarding the functionality of inspection system 100, as well as display, in real-time or otherwise, the results of an inspection of weld 20 using inspection system 100, to show, for example, one or more discontinuities detected by inspection system 100. An operator of inspection system 100 can interact with computer 140 to control inspection system 100 and to carry out any functionality related thereto.

Computer 140 may operate in a logical fashion to perform operations, execute control algorithms, store and retrieve data, and perform other desired operations. Computer 140 may include or access memory, secondary storage devices, processors, and any other components for running a program. The memory and secondary storage devices may be in the form of read-only memory (ROM) or random access memory (RAM) or integrated circuitry that is accessible by computer 140. Computer 140 may be a single computer or may include more than one computer disposed to control various functions and/or features of inspection system 100, wherein any of the one or more computers may be disposed remotely from inspection system 100. The term "computer" is meant to be used in its broadest sense to include one or more computers and/or microprocessors that may be associated with inspection system 100 and that may cooperate in controlling various functions and operations of inspection system 100. The functionality of the computer 140 may be implemented in hardware and/or software without regard to the functionality. Although computer 140 is shown as a laptop computer, computer 140 could be a desktop computer, a tablet, a portable scanning device, or another mobile device, such as a smartphone, or any combination thereof.

FIGS. 3-9 demonstrate how inspection system 100 may carry out a method of inspecting a weld on a component. Referring to FIG. 3, camera 110 optically senses a weld position 30 of weld 20 with respect to component 10. Optically sensing weld position 30 makes weld position 30 known to inspection system 100 such that inspection system 100 understands the orientation of weld 20 with respect to component 10. The image or video recorded by camera 110 may be displayed on computer 140.

Referring to FIG. 4, once weld position 30 is detected by camera 110 and relayed to computer 140, weld position 30 is known to inspection system 100. Based on weld position 30, projector 120 projects a primary scan path 150 on to component surface 18 of component 10. Although primary scan path 150 is shown in FIG. 4 to be to the right of weld 20, primary scan path 150 could also be projected to the left of weld 20 or elsewhere on component 10 with respect to weld 20. Primary scan path 150 has a primary scan path start point 152 and a primary scan path end point 154.

In addition to projecting on to component 10 one or more scan paths for imaging probe 130, such as primary scan path 150, computer 140 can control projector 120 so as to project other projections on to component 10. For example, projector 120 may project inspection instructions 160 on to component 10. Inspection instructions 160 may include information that is useful to the operator of inspection system 100. For example, in FIG. 4, for example, inspection instructions 160 include a plurality of arrows that show in which direction along primary scan path 150 an operator of inspection system 100 should move imaging probe 130. Inspection instructions 160 could convey different information to the operator of inspection system 100, such as what particular make and model of imaging probe 130 to use to scan weld 20, or how much time should be taken to complete a scan of weld 20 using imaging probe 130 for a given scan path. It is contemplated that projector 120 could project as inspection instructions 160 other kinds of information that would facilitate the inspection of weld 20.

Figures 5, 6:
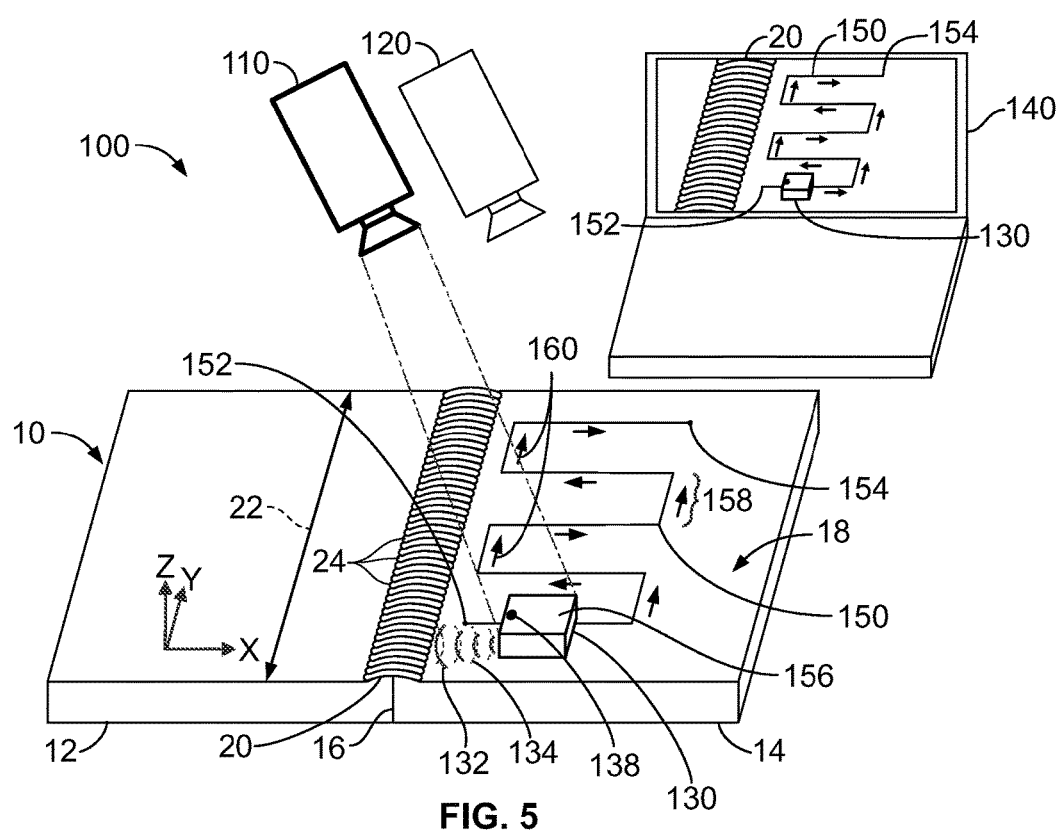
FIG. 5 is a schematic perspective view of the inspection system of FIG. 2 scanning the weld of FIG. 1 using an imaging probe.
FIG. 6 is an exemplary 2D cross-sectional image of a cross-section of the weld of FIG. 1 obtained by scanning the weld.

Referring to FIG. 5, as a general matter, a scanning operation of weld 20 is performed by moving imaging probe 130 along the primary scan path 150 projected by projector 120. More specifically, imaging probe 130 is placed on component surface 18 of component 10 at primary scan path start point 152 then moved along primary scan path 150 in the direction shown by inspection instructions 160 until imaging probe 130 reaches primary scan path end point 154. In this manner, imaging probe 130 traverses a length 22 of weld 20.

As imaging probe 130 travels along primary scan path 150, imaging probe 130 samples each cross-section 24 of weld 20. During this scanning operation, imaging probe 130 generates a plurality of 2D cross-sectional images of weld 20, each of which corresponds to a single cross-section 24 of weld 20. A sample 2D cross-sectional image 26 of a single cross-section 24 is shown in FIG. 6. 2D cross-sectional image 26 may include one or more discontinuities 28.

Turning back to FIG. 5, to generate 2D cross-sectional image 26 of cross section 24 of weld 20, imaging probe 130 emits an interrogation signal 132 in the direction of a cross-section 24. Weld 20 then reflects interrogation signal 132 back in the direction of imaging probe 130 as an echo 134. Based on echo 134, imaging probe 130 generates a signal that is representative of the characteristics of cross-section 24. This signal is converted by either imaging probe 130 or computer 140 into 2D cross-sectional image 26, such that the operator of inspection system 100 can evaluate cross-section 24 to determine, for example, if it contains one or more discontinuities such as discontinuities 28. The interrogation/echo process can be carried out along a length 22 of weld 20 so as to generate a 2D cross-sectional image 26 for each cross-section 24 of weld 20. In this manner, imaging probe 130 may be used to scan weld 20 so as to generate information used to determine whether weld 20 includes one or more discontinuities 28. The plurality of 2D cross-sectional images 26 may be provided to computer 140 for analysis.

As imaging probe 130 moves along primary scan path 150, the position of imaging probe 130 with respect to weld 20 varies in the X- and Y-directions. In particular, during scanning of weld 20, imaging probe 130 can translate in the X- and Y-directions with respect to component surface 18 (i.e., parallel to the plane defined by component surface 18) such that imaging probe 130 has an imaging probe position 156 that varies as imaging probe 130 travels along primary scan path 150. Imaging probe position 156 may be defined using, for example, the X- and Y-coordinate system shown in FIG. 5. Imaging probe position 156 may also have a component in the Z-axis (which projects perpendicularly from component surface 18 of component 10, as shown in FIG. 5) if component surface 18 of component 10 is not flat.

By way of background, the likelihood of finding one or more discontinuities 28 in weld 20 is increased if the interrogation signal 132 emitted by imaging probe 130 is perpendicularly incident on weld 20 (i.e., if imaging probe 130 is oriented such that interrogation signal 132 intersects the weld at a 90° angle), as shown in FIG. 5. If imaging probe 130 is oriented such that interrogation signal 132 is perpendicularly incident on weld 20, imaging probe 130 is said to be at a 0° skew angle with respect to weld 20.

Figure 7:
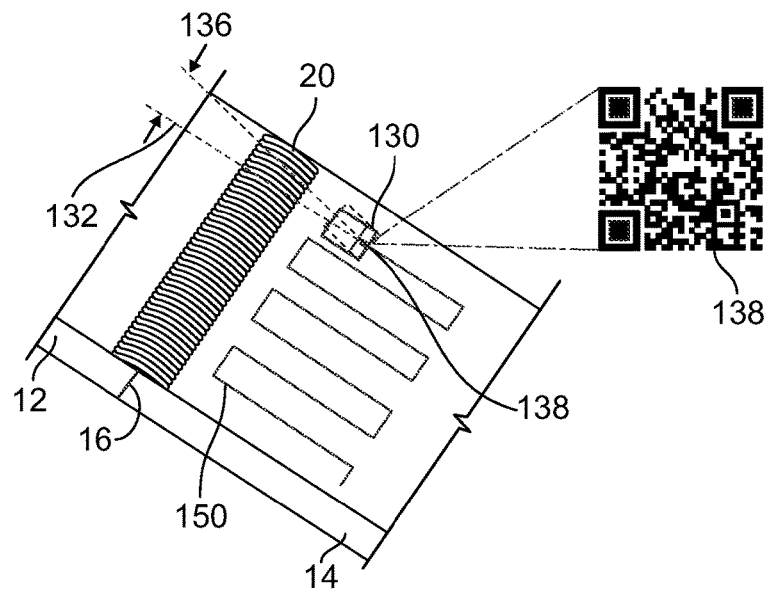
FIG. 7 is a schematic top perspective view of the imaging probe of FIG. 5 at a position and skew angle with respect to the weld of FIG. 1.

However, during the scanning operation, imaging probe 130 may rotate with respect to the Z-axis, as shown in FIG. 7. In particular, during scanning of weld 20, imaging probe 130 may rotate such that imaging probe 130 has an imaging probe skew angle 136 that varies as imaging probe 130 travels along the scan path, such as primary scan path 150. Rotation of imaging probe 130 may result, for example, from the movement of imaging probe 130 by the operator of inspection system 100. If during movement along the scan path imaging probe 130 rotates clockwise a small amount with respect to the Z-axis such that interrogation signal 132 is not perpendicularly incident on weld 20, imaging probe 130 is at a positive imaging probe skew angle 136 with respect to weld 20. FIG. 7 shows an imaging probe skew angle 136 of approximately 15°. Imaging probe skew angle 136 may be defined based on the coordinate system for imaging probe position 156, or, alternatively, on some other coordinate system. Furthermore, imaging probe skew angle 136 could have values between 0° and 360°, or could have values between −180° and 180°.

To monitor imaging probe position 156 and imaging probe skew angle 136, which vary as imaging probe 130 traverses a scan path, imaging probe 130 may include a position and skew angle indicator 138. Position and skew angle indicator 138 may be disposed on a top surface of imaging probe 130. Position and skew angle indicator 138 may be, for example, a QR code (as shown in FIG. 7) or a bar code, although it is contemplated that other types of positional/orientation indicators may be used. Position and skew angle indicator 138 is visible to camera 110 such that camera 110 is able to ascertain both the imaging probe position 156 of imaging probe 130 with respect to weld 20 and the imaging probe skew angle 136 of imaging probe 130 with respect to weld 20 as imaging probe 130 traverses a scan path projected on to component 10 by projector 120.

Turning back to FIG. 5, camera 110 optically senses position and skew angle indicator 38 as imaging probe 130 moves along (primary scan path 150. In this manner, camera 110 optically encodes each 2D cross-sectional image 26 sampled by imaging probe 130 at each cross-section 24 of weld 20 with both the imaging probe position 156 of imaging probe 130 and the imaging probe skew angle 136 of imaging probe 130 associated with that cross-section 24. This process is carried out for each cross-section 24 of weld 20 so as to generate a plurality of 2D cross-sectional images 26, each of which is encoded with a respective imaging probe position 156 and a respective imaging probe skew angle 136.

The plurality of 2D cross-sectional images 26 may be analyzed by one or more programs run on computer 140 or by the operator of inspection system 100 to determine whether it does not include a 2D cross-sectional image 26 for one or more cross-sections 24 of weld 20. The analysis may be performed in real-time or otherwise. In some cases, imaging probe 130 may not generate a 2D cross-sectional image 26 for one or more cross-sections 24 of weld 20 despite imaging probe 130 scanning the length 22 of weld 20, whether due to operator error or some other error. In particular, an error may cause imaging probe 130 not to acquire data for one or more of the scanned cross-sections 24 such that a 2D cross-sectional image is not generated for the one or more cross-sections 24.

If the plurality 2D cross-sectional images 26 of weld 20 does not include a 2D cross-sectional image 26 for one or more cross-sections 24 of weld 20, weld 20 may be rescanned. Rescanning weld 20 helps to ensure that the plurality of 2D cross-sectional images 26 of weld 20 includes a 2D cross-sectional image 26 for all cross-sections 24 of weld 20.

The rescanning of weld 20 may be performed in various ways. For example, weld 20 may be rescanned by moving imaging probe 130 along a subset 158 of primary scan path 150, as shown in FIG. 5. Subset 158 is coincident with primary scan path 150 but not coextensive. For example, subset 158 may be a short linear portion of primary scan path 150 that runs parallel to length 22 of weld 20 (as shown in FIG. 5), or may be a single point along primary scan path 150. In either case, subset 158 corresponds to one or more cross-sections 24 of weld 20 for which there was no 2D cross-sectional image 26 in the plurality of 2D cross-sectional images 26 generated by the scanning along primary scan path 150.

Figure 8:
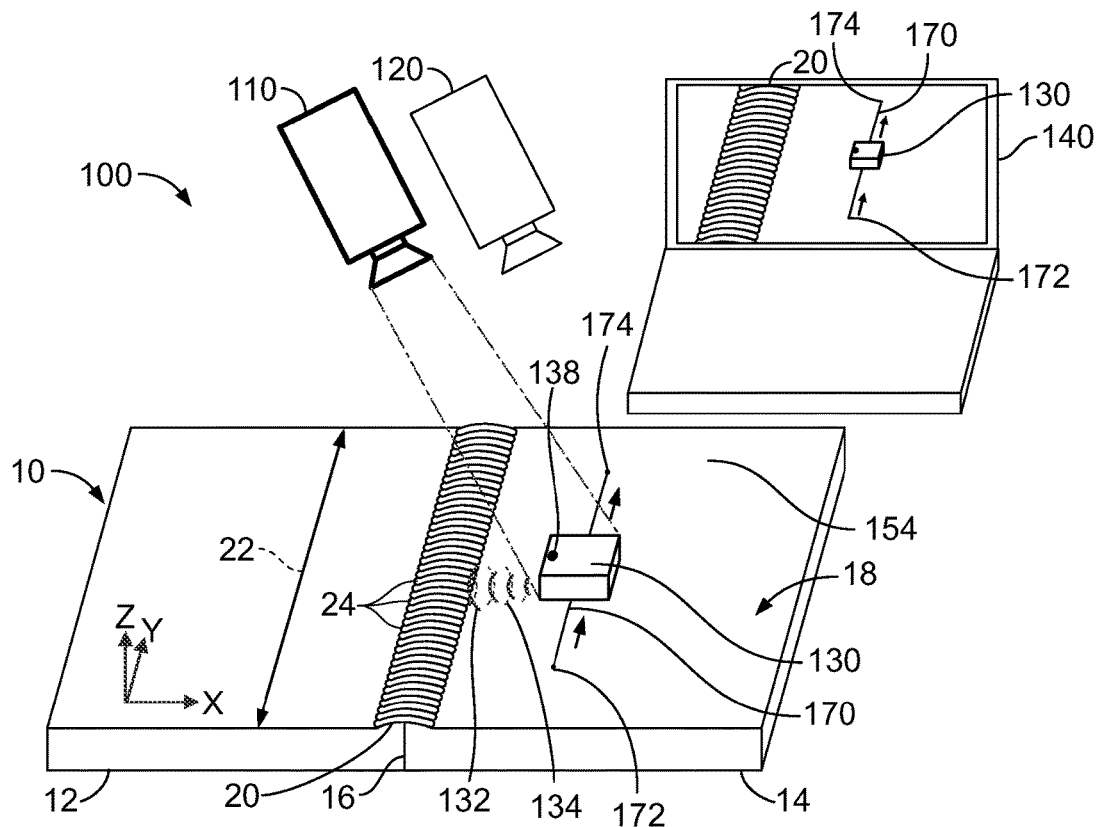
FIG. 8 is a schematic perspective view of the inspection system of FIG. 2 projecting a different scan path on to the component of FIG. 1.

As shown in FIG. 8, weld 20 may also be rescanned using a scan path other than primary scan path 150. For example, projector 120 may cease projecting primary scan path 150 on to component 10 and may instead project a secondary scan path 170 thereon. To rescan weld 20, imaging probe 130 is moved along secondary scan path 170 from secondary scan path start point 172 to secondary scan path end point 174. Like subset 158, secondary scan path 170 corresponds to one or more cross-sections 24 of weld 20 for which no 2D cross-sectional image 26 was generated during the scanning along primary scan path 150.

As with the scanning operation performed along primary scan path 150, during rescanning, whether using subset 158 or secondary scan path 170, imaging probe 130 has an imaging probe position 156 with respect to weld 20 and an imaging probe skew angle 136 with respect to weld 20, both of which vary during the rescanning operation. Camera 110 optically encodes each supplemental 2D cross-sectional image 26 sampled by imaging probe 130 at each cross-section 24 of weld 20 with a respective imaging probe position 156 of imaging probe 130 and a respective imaging probe skew angle 136 of imaging probe 130 associated with that cross-section 24. In this manner, rescanning weld 20 by moving imaging probe 130 either along subset 158 or from secondary scan path start point 172 to secondary scan path end point 174 generates supplemental 2D cross-sectional images 26 that correspond to the one or more cross-sections 24 not included in the plurality of 2D cross-sectional images 26 generated as imaging probe 130 traversed primary scan path 150. The supplemental 2D cross-sectional images 26 may then be incorporated into the plurality of 2D cross-sectional images 26 based on the respective imaging probe position 156 and the respective imaging probe skew angle 136 for each supplemental 2D cross-sectional image 26, as optically encoded by camera 110.

The plurality of 2D cross-sectional images 26, which includes 2D cross-sectional images 26 for each cross section 24 of weld 20, may be provided to computer 140 for analysis. For example, computer 140 may be used to integrate the plurality of 2D cross-sectional images 26 of weld 20 into a 3D weld discontinuity overlay. The 3D weld discontinuity overlay is a 3D representation of the discontinuity information collected by imaging probe 130 and optically encoded by camera 110 during the scanning, and if necessary the rescanning, of weld 20.

The 3D weld discontinuity overlay may be superimposed on a 3D representation of component 10 stored on computer 140 so as to create a 3D discontinuity representation of component 10. By superimposing the 3D weld discontinuity overlay on to a 3D representation of component 10, any discontinuities detected by inspection system 100 on component 10 may be seen in the context of component 10. More specifically, the 3D discontinuity representation of component 10 can be analyzed (in real-time or otherwise) to determine whether weld 20 includes one or more discontinuities, and if so, whether such discontinuities are acceptable or rejectable. The analysis can be performed by one or more programs running on computer 140 and/or manually by the operator of inspection system 100. In this manner, an inspector can more easily ascertain the locations of any rejectable discontinuities of the weld 20 on component 10.

Figure 9:
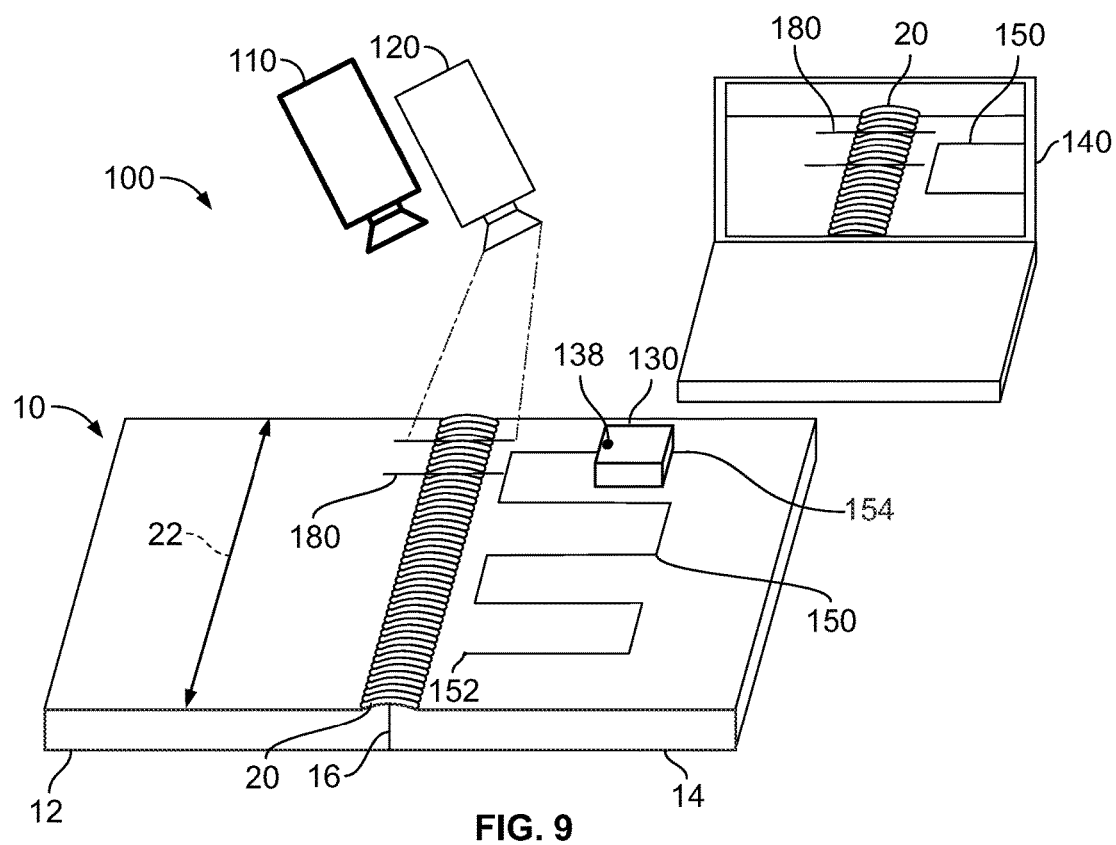
FIG. 9 is a schematic perspective view of the inspection system of FIG. 2 identifying a rejectable discontinuity on the weld of FIG. 1.

Turning to FIG. 9, if one or more discontinuities 28 in the 3D discontinuity representation of component 10 is rejectable, projector 120 can project a location 180 of the rejectable discontinuity on to weld 20. In this manner, the location 180 of the rejectable discontinuity is apparent to the operator of inspection system 100. The operator can then transcribe location 180 of the rejectable discontinuity on to the weld 20 or on to component 10 (e.g., with a removable indicator, a grease pencil, a marker, or the like) so that component 10 may be provided to a welder who can fix the rejectable discontinuity.

Figure 10:
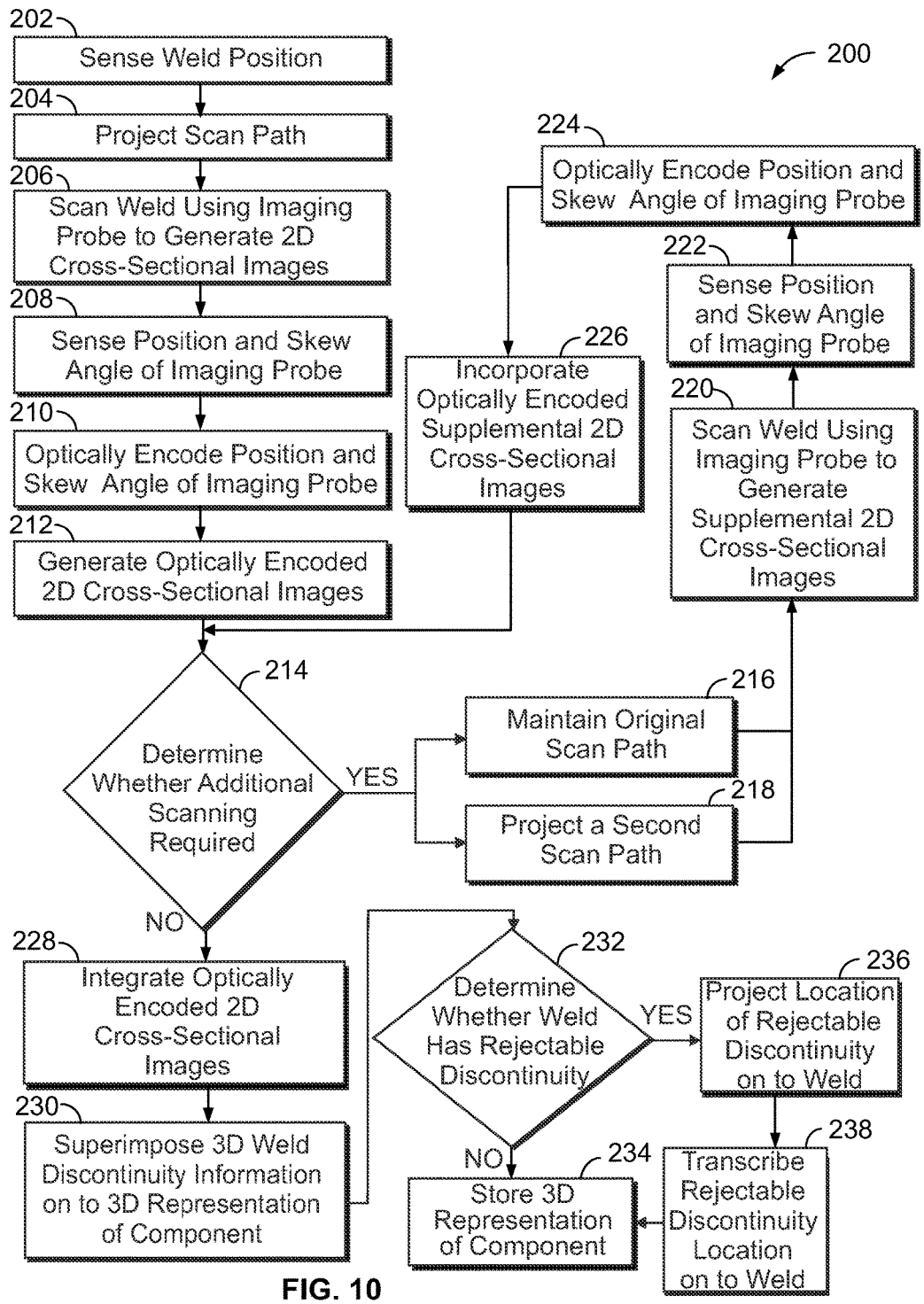
FIG. 10 is a flow chart illustrating an exemplary inspection method according to the present disclosure.

FIG. 10 is a flow chart of a method 200 of inspecting weld 20 on component 10 using the inspection system 100 shown in FIGS. 2-9. At step 202, a weld position 30 of weld 20 with respect to component 10 is optically sensed by camera 110. At step 204, projector 120 projects a primary scan path 150 on to component 10 along a length 22 of weld 20. Primary scan path 150 has a primary scan path start point 152 and a primary scan path end point 154. At step 206, imaging probe 130 is used to scan weld 20. In particular, imaging probe 130 is moved from primary scan path start point 152 to primary scan path end point 154. As imaging probe 130 moves along primary scan path 150, imaging probe 130 generates a plurality of 2D cross-sectional images 26 that correspond to the cross-sections 24 of weld 20. At the same time, as shown in step 208, camera 110 optically senses an imaging probe position 156 of imaging probe 130 with respect to weld 20 as well as imaging probe skew angle 136 of imaging probe 130 with respect to weld 20. For each 2D cross-sectional image 26 of cross-section 24 generated by imaging probe 130 in step 206, camera 110 optically encodes a respective imaging probe position 156 of imaging probe 130 and a respective imaging probe skew angle 136 of imaging probe 130 that corresponds to the cross-section 24, as shown in step 210. This generates a plurality of 2D cross-sectional images 26, each of which is optically encoded with the respective imaging probe position 156 and respective imaging probe skew angle 136 that corresponds to that cross-section 24, as shown in step 212. The optical encoding performed in step 212 associates each 2D cross-sectional image 26 with the imaging probe position 156 and imaging probe skew angle 136 that corresponds to the cross-section 24 used to generate that 2D cross-sectional image 26.

At step 214, either one or more programs run on computer 140 or the operator of inspection system 100 determines whether additional scanning of weld 20 is needed. Additional scanning or rescanning of weld 20 may be needed if the plurality of 2D cross-sectional images 26 generated in step 206 does not include a 2D cross-sectional image 26 for one or more of cross-sections 24 of weld 20. In the event that additional scanning or rescanning of weld 20 is required, projector 120 either continues to project primary scan path 150 on to component 10, as shown in step 216, or will cease projecting primary scan path 150 and instead project secondary scan path 170 on to component 10, as shown in step 218.

In the case of step 216, projector 120 continues to project primary scan path 150 on to component 10. However, instead of moving imaging probe 130 from primary scan path start point 152 to primary scan path end point 154 along primary scan path 150, as in step 206, imaging probe 130 is instead moved along a subset 158 of primary scan path 150, as shown in FIG. 5. Subset 158 corresponds to one or more cross-sections 24 of weld 20 for which there was no 2D cross-sectional image 26 in the plurality of 2D cross-sectional images 26 generated by the scanning along primary scan path 150 performed in step 206.

In the case of step 218, projector 120 ceases projecting primary scan path 150 on to component 10 and instead projects on to component 10 a secondary scan path 170 with a secondary scan path start point 172 and a secondary scan path end point 174. Like subset 158, secondary scan path 170 corresponds to one or more cross-sections 24 of weld 20 for which no 2D cross-sectional image 26 was generated during the scanning along primary scan path 150 performed in step 206.

In step 220, imaging probe 130 is then moved along primary scan path 150, in the case of step 216, or along secondary scan path 170, as in the case of step 218, to generate supplemental 2D cross-sectional images 26 for those cross-sections 24 of weld 20 for which the scan in step 206 did not generate a cross-sectional image 26. For each supplemental 2D cross-sectional image 26 of cross-section 24 generated by imaging probe 130 in step 220, camera 110 optically encodes a respective imaging probe position 156 of imaging probe 130 and a respective imaging probe skew angle 136 of imaging probe 130 that correspond to the cross-section 24, as shown in step 222. This generates supplemental 2D cross-sectional images 26 of weld 20, each of which is optically encoded with the respective imaging probe position 156 and respective imaging probe skew angle 136 that corresponds to that cross-section 24, as shown in step 224. In step 226, the supplemental 2D cross-sectional images 26 generated in step 220 are incorporated into the plurality of 2D cross-sectional images 26 of weld 20 generated in step 212 based on the respective imaging probe position 156 and respective imaging probe skew angle 136 for each supplemental 2D cross-sectional image 26 optically encoded in step 224.

The plurality of optically encoded 2D cross-sectional images 26 (whether generated in step 212 or generated in step 212 and then supplemented in step 226) can be integrated into a 3D weld discontinuity overlay, as shown in step 228. In step 230, the 3D weld discontinuity overlay can be superimposed on a 3D representation of component 10 that is stored on computer 140 in order to generate a 3D discontinuity representation of component 10. In step 232, the 3D discontinuity representation of component 10 can be analyzed (in real-time or otherwise) to determine whether weld 20 includes one or more discontinuities, and if so, whether such discontinuities are acceptable or rejectable. The analysis can be performed by one or more programs running on computer 140 and/or manually by the operator of inspection system 100. In this manner, an inspector can more easily ascertain the locations of any rejectable discontinuities of the weld 20 on component 10.

In the event that the 3D discontinuity representation of component 10 does not include one or more discontinuities 28, or it is determined that all such discontinuities are acceptable, the 3D discontinuity representation of component 10 can be stored on computer 140, as shown in step 234. In the event that the 3D discontinuity representation of component 10 does include a rejectable discontinuity, in step 236 projector 120 projects a location 180 of the rejectable discontinuity onto weld 20, as shown in FIG. 9. The operator of inspection system 100 can then transcribe the location 180 of the rejectable discontinuity on to weld 20 so as, for example, to indicate to a welder the location 180 on weld 20 that requires additional welding or rewelding, as shown in step 238. Then, in step 234, the 3D discontinuity representation of component 10, which includes the location 180 of the rejectable discontinuity, can be stored on computer 140. In this manner, a record of the rejectable discontinuity and its location 180 on weld 20 can be saved for future reference.

INDUSTRIAL APPLICABILITY

In general, the methods and systems of inspecting a weld of the present disclosure are applicable for use in various industrial applications, such as non-destructive weld evaluation. The methods and systems may be used to inspect welds on any component that includes one or more welds, for example at a time when the component is manufactured, for routine quality inspections, or for diagnosis when the component has failed or started to fail.

Inspecting a component according to the methods of or with the systems of the present disclosure may provide a reliable means of gathering and recording relevant encoded data collected by an imaging probe during a scanning operation. More specifically, the disclosed methods and systems may provide an objective, repeatable technique for assessing whether a weld includes one or more discontinuities. If the inspection technique is Objective and repeatable, the level of training required for an operator to use the inspection methods and systems of the present disclosure may be reduced, and operating costs may correspondingly decrease.

This disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method of inspecting a weld on a component, the weld having a plurality of cross-sections, the method comprising:

optically sensing a weld position of the weld with respect to the component;

projecting on to the component along a length of the weld position a primary scan path with a primary scan path start point and a primary scan path end point;

scanning the weld by moving an imaging probe from the primary scan path start point to the primary scan path end point so as to generate a plurality of 2D cross-sectional images of the weld that correspond to the plurality of cross-sections of the weld, the imaging probe having an imaging probe position with respect to the weld and an imaging probe skew angle with respect to the weld, both of which vary as the imaging probe moves along the primary scan path;

optically encoding for each of the plurality of 2D cross-sectional images of the weld a respective imaging probe position and a respective imaging probe skew angle of the imaging probe;

analyzing the plurality of 2D cross-sectional images of the weld so as to determine whether it does not include a 2D cross-sectional image for one or more cross-sections of the weld; and rescanning the weld if the plurality of 2D cross-sectional images of the weld does not include a 2D cross-sectional image for one or more cross-sections of the weld, wherein, if the plurality of 2D cross-sectional images of the weld does not include a 2D cross-sectional image for one or more of the plurality of cross-sections of the weld, the method further comprises:

rescanning the weld by moving the imaging probe along a subset of the primary scan path that corresponds to the one or more cross-sections for which the plurality of 2D cross-sectional images of the weld does not include a 2D cross-sectional image and scanning at least the one or more cross-sections so as to generate supplemental 2D cross-sectional images thereof;

optically encoding for each of the supplemental 2D cross-sectional images a respective imaging probe position and a respective imaging probe skew angle of the imaging probe; and incorporating the supplemental 2D cross-sectional images into the plurality of 2D cross-sectional images based on the respective imaging probe position and respective imaging probe skew angle for each supplemental 2D cross-sectional image.

2. The method of claim 1, wherein, if the plurality of 2D cross-sectional images of the weld does not include a 2D cross-sectional image for one or more of the plurality of cross-sections of the weld, the method further comprises:

projecting on to the component along the length of the weld position a secondary scan path with a secondary scan path start point and a secondary scan path end point, the secondary scan path corresponding to the one or more cross-sections for which the plurality of 2D cross-sectional images of the weld does not include a 2D cross-sectional image;

rescanning the weld by moving the imaging probe from the secondary scan path start point to the secondary scan path end point and scanning at least the one or more cross-sections of the weld for which the plurality of 2D cross-sectional images of the weld does not include a 2D cross-sectional image so as to generate supplemental 2D cross-sectional images thereof, the imaging probe having an imaging probe position with respect to the weld and an imaging probe skew angle with respect to the weld, both of which vary as the imaging probe moves along the secondary scan path;

optically encoding for each of the supplemental 2D cross-sectional images a respective imaging probe position and a respective imaging probe skew angle of the imaging probe; and incorporating the supplemental 2D cross-sectional images into the plurality of 2D cross-sectional images based on the respective imaging probe position and respective imaging probe skew angle for each supplemental 2D cross-sectional image.

3. The method of claim 1, further comprising:

integrating the plurality of 2D cross-sectional images of the weld into a 3D weld discontinuity overlay.

4. The method of claim 3, further comprising:

superimposing the 3D weld discontinuity overlay on to a 3D representation of the component to create a 3D discontinuity representation of the component.

5. The method of claim 4, further comprising:

storing the 3D discontinuity representation of the component on a computer.

6. The method of claim 4, further comprising:

analyzing the 3D discontinuity representation of the component to determine whether the weld includes one or more rejectable discontinuities.

7. The method of claim 6, wherein, if the weld includes one or more rejectable discontinuities, the method further comprises:

projecting a location of the one or more rejectable discontinuities on to the weld.

8. The method of claim 7, further comprising:

transcribing on to the weld the location of the one or more rejectable discontinuities that is projected on to the weld.

9. The method of claim 1, further comprising:

projecting inspection instructions on to the component.

10. The method of claim 1, wherein the steps of optically sensing the weld position and optically encoding for each of the plurality of 2D cross-sectional images of the weld the respective imaging probe position and the respective imaging probe skew angle of the imaging probe are performed by a camera.

11. A method of inspecting a weld on a component, the weld having a plurality of cross-sections, the method comprising:

optically sensing a weld position of the weld with respect to the component;

projecting on to the component along a length of the weld position a primary scan path with a primary scan path start point and a primary scan path end point;

scanning the weld by moving an imaging probe from the primary scan path start point to the primary scan path end point so as to generate a plurality of 2D cross-sectional images of the weld that correspond to the plurality of cross-sections of the weld, the imaging probe having an imaging probe position with respect to the weld and an imaging probe skew angle with respect to the weld, both of which vary as the imaging probe moves along the primary scan path;

optically encoding for each of the plurality of 2D cross-sectional images of the weld a respective imaging probe position and a respective imaging probe skew angle of the imaging probe;

analyzing the plurality of 2D cross-sectional images of the weld so as to determine whether it does not include a 2D cross-sectional image for one or more cross-sections of the weld; and rescanning the weld if the plurality of 2D cross-sectional images of the weld does not include a 2D cross-sectional image for one or more cross-sections of the weld, wherein, if the plurality of 2D cross-sectional images of the weld does not include a 2D cross-sectional image for one or more of the plurality of cross-sections of the weld, the method further comprises:

projecting on to the component along the length of the weld position a secondary scan path with a secondary scan path start point and a secondary scan path end point, the secondary scan path corresponding to the one or more cross-sections for which the plurality of 2D cross-sectional images of the weld does not include a 2D cross-sectional image;

rescanning the weld by moving the imaging probe from the secondary scan path start point to the secondary scan path end point and scanning at least the one or more cross-sections of the weld for which the plurality of 2D cross-sectional images of the weld does not include a 2D cross-sectional image so as to generate supplemental 2D cross-sectional images thereof, the imaging probe having an imaging probe position with respect to the weld and an imaging probe skew angle with respect to the weld, both of which vary as the imaging probe moves along the secondary scan path;

optically encoding for each of the supplemental 2D cross-sectional images a respective imaging probe position and a respective imaging probe skew angle of the imaging probe; and incorporating the supplemental 2D cross-sectional images into the plurality of 2D cross-sectional images based on the respective imaging probe position and respective imaging probe skew angle for each supplemental 2D cross-sectional image.

12. The method of claim 11, further comprising integrating the plurality of 2D cross-sectional images of the weld into a 3D weld discontinuity overlay.

13. The method of claim 12, further comprising superimposing the 3D weld discontinuity overlay on to a 3D representation of the component to create a 3D discontinuity representation of the component.

14. The method of claim 13, further comprising storing the 3D discontinuity representation of the component on a computer.

15. The method of claim 13, further comprising analyzing the 3D discontinuity representation of the component to determine whether the weld includes one or more rejectable discontinuities.

16. The method of claim 15, wherein, if the weld includes one or more rejectable discontinuities, the method further comprises projecting a location of the one or more rejectable discontinuities on to the weld.

17. The method of claim 16, further comprising transcribing on to the weld the location of the one or more rejectable discontinuities that is projected on to the weld.

18. The method of claim 11, further comprising projecting inspection instructions on to the component.

19. The method of claim 11, wherein the steps of optically sensing the weld position and optically encoding for each of the plurality of 2D cross-sectional images of the weld the respective imaging probe position and the respective imaging probe skew angle of the imaging probe are performed by a camera.

* * * * *